United States Patent [19]

Miyazawa et al.

[11] Patent Number: 5,015,283

[45] Date of Patent: May 14, 1991

[54] PLANT GROWTH REGULATING COMPOSITION AND METHOD FOR REGULATING GROWTH OF A PLANT

[75] Inventors: Takeshige Miyazawa, Shizuoka; Kazuhiko Kawano, Niiza, both of Japan

[73] Assignee: Kumiai Chemical Industry Co., Ltd., Tokyo, Japan

[21] Appl. No.: 521,894

[22] Filed: Apr. 10, 1990

Related U.S. Application Data

[62] Division of Ser. No. 353,550, May 18, 1989, Pat. No. 4,954,157.

[30] Foreign Application Priority Data

May 19, 1988 [JP] Japan .................. 63-122268

[51] Int. Cl.$^5$ ............ A01N 31/06; A01N 33/04; A01N 43/40
[52] U.S. Cl. ............................. 71/76; 71/65; 71/94; 71/121; 71/106
[58] Field of Search ............ 71/65, 76, 94, 121

[56] References Cited

U.S. PATENT DOCUMENTS

| | | | |
|---|---|---|---|
| 3,905,798 | 9/1975 | Zeeh et al. | 71/76 |
| 4,560,403 | 12/1985 | Motojima et al. | 71/106 |
| 4,678,496 | 7/1987 | Motojima et al. | 71/76 |

OTHER PUBLICATIONS

The Pesticide Manual, 8th Ed., pp. 346-347, p. 529, and pp. 158-159.
The Agrochemicals Handbook ed. Douglas Hartley Royd Society of Chemistry, 1983.

*Primary Examiner*—Richard L. Raymond
*Assistant Examiner*—B. Bembenick
*Attorney, Agent, or Firm*—Oblon, Spivak, McClelland, Maier & Neustadt

[57] ABSTRACT

A plant growth regulating composition comprising a member selected from the group consisting of 3,5-dioxo-4-propionylcyclohexane carboxylic acid and its esters and salts, represented by the formula:

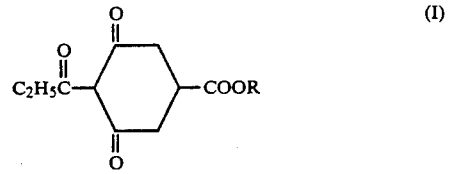

wherein R is a hydrogen atom, a lower alkyl group or a cation, and at least one compound selected from the group consisting of (2-chloroethyl) phosphonic acid, 1,1-dimethylpiperidinium chloride and 2-chloroethyltrimethylammonium chloride, as active ingredients, and an agricultural carrier or diluent.

6 Claims, No Drawings

PLANT GROWTH REGULATING COMPOSITION AND METHOD FOR REGULATING GROWTH OF A PLANT

This is a division of application Ser. No. 07/353,550, filed May 18, 1989, now U.S. Pat. No. 4,954,157.

The present invention relates to a plant growth regulating composition and a method of its use.

Heretofore, various plant growth regulating agents have been known. For example, 3,5-dioxo-4propionyl-cyclohexane carboxylic acid derivatives are known to control the growth of various plants (U.S. Pat. Nos. 4,560,403 and 4,678,496). Further, (2chloroethyl) phosphonic acid (hereinafter referred to as Compound A), 1,1-dimethylpiperidinium chloride (hereinafter referred to as Compound B) and 2chloroethyltrimethylammonium chloride (hereinafter referred to as Compound C) are known, respectively, as plant growth regulating agents (The Pestside Manual, 8th edition, p. 346–347, p. 529 and p. 158–159).

However, when these compounds are used alone, it is not necessarily possible to obtain various plant growth regulating activities. For example, they are likely to present phytotoxicity or kill the plants due to a change in the weather conditions at the time of their use or in the growing conditions of the plants. Therefore, it is desired to develop a plant growth regulating agent which exhibits strong plant growth regulating activities at a low dose and provides stabilized effects constantly without being influenced by various factors for influencing the activities and which is highly safe to plants.

As a result of extensive researches for developing a plant growth regulating agent to fullfill such requirements, the present inventors have found that the plant growth regulating composition of the present invention solves the above-mentioned problems and have accomplished the present invention.

The present invention provides a plant growth regulating composition comprising a member selected from the group consisting of 3,5-dioxo-4-propionylcyclohexane carboxylic acid and its esters and salts, represented by the formula:

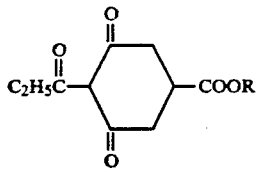
(I)

wherein R is a hydrogen atom, a lower alkyl group or a cation, and at least one compound selected from the group consisting of (2-chloroethyl) phosphonic acid, 1,1-dimethylpiperidinium chloride and 2-chloroethyltrimethylammonium chloride, as active ingredients, and an agricultural carrier or diluent.

The present invention also provides a method for regulating growth of a plant, which comprises applying such plant regulating composition to the plant.

Further, the present invention provides a method for regulating growth of a plant, which comprises formulating said member and said at least one compound separately, mixing the formulations prior to or at the time of use, and applying the mixture to the plant.

Now, the present invention will be described in detail with reference to the preferred embodiments.

The esters of 3,5-dioxo-4-propionylcyclohexane carboxylic acid include, for example, methyl, ethyl, propyl, isopropyl and butyl esters. Likewise, the salts thereof include alkali metal salts, alkaline earth metal salts and amine salts, such as sodium, potassium, calcium, diethanol amine, diethylamine and propylamine salts.

Specific examples of said member include the following compounds:

Compound 1: 3,5-dioxo-4-propionylcyclohexane carboxylic acid

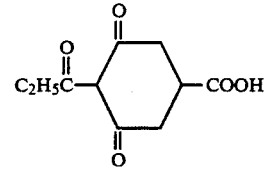

Compound 2: Ethyl 3,5-dioxo-4-propionylcyclohexane carboxylate

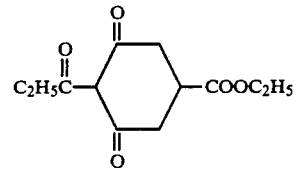

Compound 3: Propyl 3,5-dioxo-4-propionylcyclohexane carboxylate

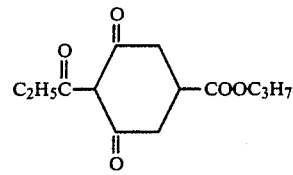

Compound 4: Calcium 3,5-dioxo-4-propionylcyclohexane carboxylate

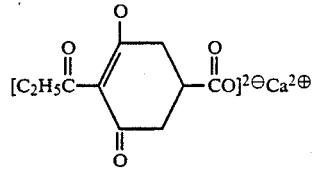

The blending ratio of such a 3,5-dioxo-4-propionylcyclohexane carboxylic acid derivative (said member) to other compounds (said at least one compound) is generally 1:0.5–50 by weight, specifically 1:0.2–20 by weight in the case of Compound A, 1:0.2–10 by weight in the case of Compound B and 1:1–50 by weight in the case of Compound C.

The proportion of the active ingredients in the composition is generally within a range of from 0.1 to 85% by weight, specifically from 1 to 75% by weight in the case of a wettable powder, from 1 to 20% by weight in the case of a granule, from 0.1 to 10% by weight in the case of a dust, from 0.5 to 50% by weight in the case of an aqueous solution, from 1 to 50% by weight in the case of a suspension, and from 1 to 85% by weight in the case of a dry flowable.

The plant growth regulating composition of the present invention may be formulated into various formulations such as a wettable powder, a granule, an emulsifiable concentrate or a dust by blending the two types of compounds with a carrier or diluent which is commonly employed for the formulation of agricultural chemicals.

As the carrier to be used for such formulation, there may be mentioned a solid carrier such as Jeeklite, talc, bentonite, clay, kaolin, diatomaceous earth, white carbon, vermiculite, slaked lime, silica sand, ammonium sulfate or urea, or a liquid carrier such as isopropyl alcohol, xylene, cyclohexanone, methylnaphthalene, acetone, isophorone, dimethylsulfoxide, acetonitrile, vegetable oil or water. As the surfactant and dispersing agent, there may be mentioned, for example, an alcohol-sulfuric acid ester, an alkyl aryl sulfonate, lignin sulfonate, a polyoxyethylene glycol ether, a polyoxyethylene alkyl aryl ether or a polyoxyethylene sorbitol mono-alkylate. As the adjuvant, for example, carboxymethyl cellulose, polyethylene glycol or gum arabic may be mentioned.

In practical use, such a formulation may be diluted to a suitable concentration before application, or may directly be applied. Further, the two kinds of compounds may be formulated separately and may be mixed at the time of use. Namely, one of Compounds 1 to 4 and at least one of Compounds A, B and C, may be separately formulated, and such formulations may be mixed and diluted at the time of practical application. In this case, Compounds 1 to 4 may be formulated into a wettable powder, a flowable, an emulsifierable concentrate or a liquid formulation containing from 5 to 80% by weight of the active ingredient, and Compounds A, B and C may be formulated into e.g. a liquid formulation containing from 10 to 60% by weight of the active ingredient. The respective formulations may be diluted to proper concentrations and then mixed and applied in a liquid form.

Further, the plant growth regulating composition of the present invention may be used in combination with an insecticide, a fungicide, a herbicide, other plant growth regulating agents or a fertilizer.

The dose of the plant growth regulating composition of the present invention varies depending upon the type of the plant to be treated, the weather condition, the type of the formulation of the composition, the blending ratio of the active ingredients, the manner of application and the timing of application. However, the dose is usually within a range of from 1 to 500 g/10 are in the total amount of the active ingredients.

Now, Formulation Examples of the plant growth regulating composition of the present invention will be given. However, it should be understood that the present invention is by no means restricted by such specific Examples. In the Formulation Examples, "%" means "% by weight".

FORMULATION EXAMPLE 1 (wettable powder)

5% of Compound 4, 5% of Compound A, 0.5% of Emulgen 810 (trademark, Kao Corporation), 0.5% of Demol N (trademark, Kao Corporation), 20% of Kunilite 201 (trademark, Kunimine Kogyo K.K.) and 69% of Jeeklite CA (trademark, Jeeklite Company Ltd.) were uniformly mixed and pulverized to obtain a wettable powder.

FORMULATION EXAMPLE 2 (wettable powder)

2% of Compound 2, 10% of Compound C, 0.5% of Emulgen 810 (trademark, Kao Corporation), 0.5% Demol N (trademark, Kao Corporation), 20% of Kunilite 201 (trademark, Kunimine Kogyo K.K.) and 67% of Jeeklite CA (trademark, Jeeklite Company Ltd.) were uniformly mixed and pulverized to obtain a wettable powder.

FORMULATION EXAMPLE 3 (wettable powder)

0.5% of Compound 2, 10% of Compound C, 0.5% of Emulgen 810 (trademark, Kao Corporation), 0.5% of Demol N (trademark, Kao Corporation), 20% of Kunilite 201 (trademark, Kunimine Kogyo K.K.) and 68.5% of Jeeklite CA (trademark, Jeeklite Company Ltd.) were uniformly mixed and pulverized to obtain a wettable powder.

FORMULATION EXAMPLE 4 (dust)

1% of Compound 2, 1% of Compound B, 5% of diatomeceous earth and 93% of clay were uniformly mixed and pulverized to obtain a dust.

FORMULATION EXAMPLE 5 (aqueous solution)

3% of Compound 1, 4% of Compound C, 3% of Emulgen 105 (trademark, Kao Corporation), 2% of diethanol amine and 88% of water were uniformly dissolved to obtain an aqueous solution.

FORMULATION EXAMPLE 6 (suspension)

10% of Compound 4, 5% of Compound B, 3% of Newcargen ST-60 (trademark, Takemoto Yushi K.K.), 2% of Demol N (trademark, Kao Corporation) and 80% of water were uniformly mixed and pulverized in a ball mill to obtain a suspension.

FORMULATION EXAMPLE 7 (dry flowable)

10% of Compound 4, 10% of Compound A, 8% of sodium lignin sulfonate, 5% of sucrose, and 67% of clay were uniformly mixed. Then, water was added thereto, and the mixture was kneaded. The kneaded product was granulated by an extrusion granulator equipped with a screen having a mesh size of 0.6 mm. The granules were dried and sieved by a screen having a mesh size of 0.5 mm to obtain a dry flowable.

The plant growth regulating activities of the plant growth regulating composition of the present invention are primarily elongation retarding activities and internode elongation retarding activities. However, various plant growth regulating activities will be obtained by changing the plant to be treated, the manner of application, the timing of application or the dose of the active ingredients. Excellent plant growth regulating effects can be obtained at a dose substantially lower than the dose in a case where the two types of compounds are used independently. By the application to the foliage of e.g. rice, wheat, barley, rye or corn, it is possible to control the internode elongation, to shorten the stem or to make the stem stout without adversely affecting the yield or quality of the product, whereby it is possible to prevent or reduce lodging due to wind or rain. Further, by the application to paddy rice, vegetables, flowers and ornamental plants, it is possible to improve the quality of seedlings and to make healthy seedlings excellent in transplantation and in the resistance against low temperature troubles. By the application at the growing stage of paddy rice, wheat, barley or rye, it is possible to shorten the length of the upper leaf or to improve the steric disposition of leaves, whereby the photo-utilization efficiency is improved and the percentage of ripened grains increases, and it is thereby possible to improve the yield and the quality of the product. Further, in the cultivation in a green house, the spindly growth can be prevented without bringing about an adverse effect even to a plant of the type wherein no adequate prevention of spindly growth can be obtained by a single use of each compound due to lack of sunlight, and thus it contributes to the improvement of the product quality. Further, the plant growth regulating composition of the present invention is capable of controlling the growth of plants in e.g. a non-agricultural field. For example, by the application to the lawn in a park, playground or road, it is possible to control the elongation or overgrowth, whereby the number of mowing operations can be reduced, or the mowing operation can be simplified.

Now, the effects obtained by the plant growth regulating composition of the present invention will be described. The test samples were formulated into wettable powders.

TEST EXAMPLE 1

In a pot filled with soil (surface area: 800 cm$^2$), seeds of barley were sown and covered with soil in a thickness of from 0.5 to 1 cm. The pot was cultured in a green house at 25° C. for 4 weeks, and then predetermined amounts of test samples were diluted with water and applied to the foliage at a rate of 100 l per 10 ares uniformly by a hand sprayer. At the time of application, the barley was at the 3-leaf stage. On the 36th day from the application, the plant length was measured, and the plant length controlling rate (%) was calculated by the following equation. Further, the phytotoxicity was investigated. The results are shown in Table 1.

Plant length controlling rate (%) =

$$\left(1 - \frac{\text{Plant length of test plant in treated area}}{\text{Plant length of test plant in non-treated area}} \times 100\right)$$

TABLE 1

| Test samples | Dose of active ingredient (g/10a) | Plant length controlling rate (%) | Phytotoxicity |
|---|---|---|---|
| Compound 2 | 40 + 40 | 46 | Nil |
| + | 40 + 20 | 29 | Nil |
| Compound A | 20 + 40 | 42 | Nil |
|  | 20 + 20 | 21 | Nil |
| Compound 2 | 80 | 16 | Nil |
|  | 40 | 11 | Nil |
|  | 20 | 8 | Nil |
| Compound A | 80 | 19 | Nil |
|  | 40 | 16 | Nil |
|  | 20 | 4 | Nil |

TEST EXAMPLE 2

In a pot filled with soil (surface area: 800 cm$^2$), seeds of barley were sown and covered with soil in a thickness of from 0.5 to 1 cm. The pot was cultured in a green house at 15° to 25° C. for 5 weeks, and then predetermined amounts of test samples were diluted with water and applied to the foliage at a rate of 100 l per 10 ares uniformly by a hand sprayer. At the time of application, the barley was at the 4-leaf stage. On the 30th day from the application, the plant length was measured, and the plant length controlling rate (%) was calculated by the following equation. Further, the phytotoxicity was investigated. The results are shown in Table 2.

Plant length controlling rate (%) =

$$\left(1 - \frac{\text{Plant length of test plant in treated area}}{\text{Plant length of test plant in non-treated area}} \times 100\right)$$

TABLE 2

| Test samples | Dose of active ingredient (g/10a) | Plant length controlling rate (%) | Phytotoxicity |
|---|---|---|---|
| Compound 4 | 40 + 80 | 48 | Nil |
| + | 40 + 40 | 46 | Nil |
| Compound A | 20 + 80 | 33 | Nil |
|  | 20 + 40 | 26 | Nil |
| Compound 4 | 80 | 30 | Nil |
|  | 40 | 26 | Nil |
|  | 20 | 13 | Nil |
| Compound A | 160 | 13 | Leaf dying, yellowing |
|  | 80 | 9 | Nil |
|  | 40 | 4 | Nil |

TEST EXAMPLE 3

In a pot filled with soil (surface area: 800 cm$^2$), seeds of wheat were sown and covered with soil in a thickness of from 0.5 to 1 cm. The pot was cultured in a green house at 15° to 25° C. for 4 weeks, and then predetermined amounts of test samples were diluted with water and applied to the foliage at a rate of 100 l per 10 ares uniformly by a hand sprayer. At the time of application, the wheat was at the 3.5-leaf stage. On the 36th day from the application, the plant length was measured, and the plant length controlling rate (%) was calculated by the following equation. Further, the phytotoxicity was investigated. The results are shown in Table 3.

Plant length controlling rate (%) =

$$\left(1 - \frac{\text{Plant length of test plant in treated area}}{\text{Plant length of test plant in non-treated area}} \times 100\right)$$

TABLE 3

| Test samples | Dose of active ingredient (g/10a) | Plant length controlling rate (%) | Phytotoxicity |
|---|---|---|---|
| Compound 2 | 20 + 40 | 26 | Nil |
| + | 20 + 20 | 22 | Nil |
| Compound B | 10 + 40 | 19 | Nil |
|  | 10 + 20 | 13 | Nil |
| Compound 2 | 40 | 15 | Nil |
|  | 20 | 10 | Nil |
|  | 10 | 5 | Nil |
| Compound B | 80 | 8 | Nil |
|  | 40 | 5 | Nil |
|  | 20 | 2 | Nil |

TEST EXAMPLE 4

In a pot filled with soil (surface area: 800 cm$^2$), seeds of wheat were sown and covered with soil in a thickness of from 0.5 to 1 cm. The pot was cultured in a green house at 15° to 25° C. for 25 days, and then predetermined amounts of test samples were diluted with water and applied to the foliage at a rate of 100 l per 10 ares uniformly by a hand sprayer. At the time of application, the wheat was at the 3-leaf stage. On the 31st day from the application, the plant length was measured, and the plant length controlling rate (%) was calculated by the following equation. Further, the phytotoxicity was investigated. The results are shown in Table 4.

Plant length controlling rate (%) =

$$\left(1 - \frac{\text{Plant length of test plant in treated area}}{\text{Plant length of test plant in non-treated area}} \times 100\right)$$

TABLE 4

| Test samples | Dose of active ingredient (g/10a) | Plant length controlling rate (%) | Phytotoxicity |
| --- | --- | --- | --- |
| Compound 2 + Compound C | 20 + 200 | 32 | Nil |
| | 20 + 100 | 27 | Nil |
| | 10 + 200 | 26 | Nil |
| | 10 + 100 | 20 | Nil |
| Compound 2 | 40 | 16 | Nil |
| | 20 | 10 | Nil |
| | 10 | 5 | Nil |
| Compound C | 400 | 15 | Nil |
| | 200 | 12 | Nil |
| | 100 | 7 | Nil |

We claim:

1. A plant growth regulating composition comprising a member selected from the group consisting of 3,5-dioxo-4-propionylcyclohexane carboxylic acid and its esters and salts, represented by the formula:

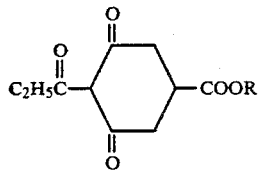

wherein R is a hydrogen atom, a lower alkyl group or a cation, and one compound selected from the group consisting of 1,1-dimethylpiperidinium chloride and 2-chloroethyltrimethylammonium chloride, as active ingredients in a ratio of 1:2.0-20 by weight, and an agricultural carrier or diluent.

2. The plant growth regulating composition according to claim 1, wherein said member is ethyl ester of 3,5-dioxo-4-nylcyclohexane carboxylic acid.

3. The plant growth regulating composition according to claim 1, which comprises calcium salt of 3,5-dioxo-4-propionylcyclohexane carboxylic acid of the formula:

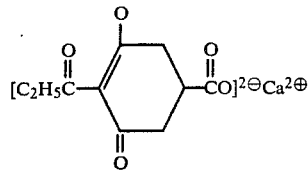

and 1,1-dimethylpiperidinium chloride.

4. The plant growth regulating composition according to claim 1, which comprises calcium salt of 3,5-dioxo-4-propionycyclohexane carboxylic acid of the formula:

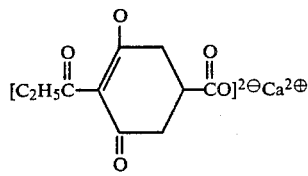

and 2-chloroethyltrimethylammonium chloride.

5. A method for controlling growth of a plant, which comprises applying an effective amount of a plant growth regulatory compositions as defined in claim 1 to the plant.

6. A method for controlling a plant, which comprises formulating a member selected from the group consisting of 3,5-dioxo-4-propionylcyclohexane carboxylic acid and its esters and salts, represented by the formula:

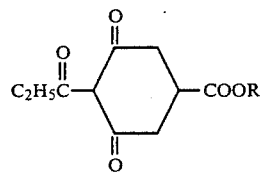

wherein R is a hydrogen atom, a lower alkyl group or a cation, and one compound selected from the group consisting of 1,1-dimethylpiperidinium chloride and 2-chloroethyltrimethyl ammonium chloride, respectively, mixing the respective formulations prior to or at the time of use, and applying the mixture to the plant in a plant growth regulatory effective amount.

* * * * *